United States Patent [19]
Pawlowski et al.

[11] Patent Number: 5,346,804
[45] Date of Patent: Sep. 13, 1994

[54] ACID-CLEAVABLE RADIATION-SENSITIVE COMPOUNDS, POSITIVE WORKING RADIATION-SENSITIVE MIXTURE CONTAINING THESES COMPOUNDS, AND RADIATION-SENSITIVE RECORDING MATERIAL PRODUCED WITH THIS MIXTURE

[75] Inventors: Geog Pawlowski, Wiesbaden, Fed. Rep. of Germany; Ralph Dammel, Coventry, R.I.; Horst Roeschert, Ober-Hilbersheim, Fed. Rep. of Germany; Walter Spiess, Dieburg, Fed. Rep. of Germany; Charlotte Eckes, Mainz, Fed. Rep. of Germany

[73] Assignee: Hoechst Aktiengesellschaft, Frankfurt am Main, Fed. Rep. of Germany

[21] Appl. No.: 871,008

[22] Filed: Apr. 20, 1992

[30] Foreign Application Priority Data

Apr. 20, 1991 [DE] Fed. Rep. of Germany ....... 4112970

[51] Int. Cl.$^5$ ............. G03C 1/73; G03C 1/725; G03F 7/025; G03F 7/027
[52] U.S. Cl. ............. 430/281; 430/270; 430/176; 430/284; 430/286; 430/292; 430/300; 430/323; 430/326; 430/914; 430/919; 430/925
[58] Field of Search ............. 430/281, 286, 270, 176, 430/326, 284, 292, 925, 300, 919, 323, 914

[56] References Cited

U.S. PATENT DOCUMENTS

| | | | |
|---|---|---|---|
| 4,101,323 | 7/1978 | Buhr et al. | 96/35 |
| 4,247,611 | 1/1981 | Sander et al. | 430/286 |
| 4,883,740 | 11/1989 | Schwalm et al. | 430/270 |
| 4,946,759 | 8/1990 | Doessel et al. | 430/270 |

FOREIGN PATENT DOCUMENTS

| | | |
|---|---|---|
| 0297443 | 1/1989 | European Pat. Off. . |
| 0315748 | 5/1989 | European Pat. Off. . |
| 0353732 | 2/1990 | European Pat. Off. . |

OTHER PUBLICATIONS

CA 116(24):245275K, "Positive Working radiation sensitive composition and radiation-sensitive recording material for exposure using UV-radiation," Roeschert, et al, Jun. 25, 1992.

Yardley et al., "Synthesis and Amebicidal Activities of Some 1',2'-Secoemetine Derivatives," *Journal of Medicinal Chemistry*, vol. 10, No. 6, pp. 1088-1091 (Nov. 1967).

Tsuji et al., "Studies on Julimycins–V: The Configurations and Conformations of Julichrome $Q_{1-3}$ amd its $C_9$-Epimer," *International Journal of Organic Chemistry*, vol. 25, No. 15, pp. 3017-3031 (Aug. 1969).

(List continued on next page.)

*Primary Examiner*—John Kight, III
*Assistant Examiner*—P. Hampton-Hightower
*Attorney, Agent, or Firm*—Foley & Lardner

[57] ABSTRACT

A radiation-sensitive mixture which contains compounds of the formula I which generate under irradiation sulfonic acids and are cleavable by the latter

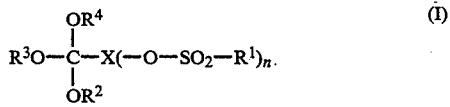

$$R^3O-\underset{\underset{OR^2}{|}}{\overset{\overset{OR^4}{|}}{C}}-X(-O-SO_2-R^1)_n. \quad (I)$$

in which
$R^1$ is an unsubstituted or substituted alkyl, fluorinated alkyl, perfluoroalkyl or aryl radical,
$R^2$ is a hydrogen atom, an unsubstituted or substituted alkyl radical, or an unsubstituted or substituted aryl radical, $(R^1-SO_2-O-)_n X-$, or $R_3O-$,
$R^3$ and $R^4$ are identical or different and are unsubstituted or substituted alkyl, cycloalkylalkyl, cycloalkenylalkyl or aralkyl radicals, in which 1 to 3 aliphatic $CH_2$ or $CH$ groups are optionally replaced by one or more of $NR^5$, O, S, CO, CO—O, CO—NH, O—CO—NH, CO—NH—CO, NH—CO—NH, $SO_2$, $SO_2$—O or $SO_2$—NH, or unsubstituted or substituted alkenyl, alkynyl, cycloalkyl or cycloalkenyl radicals, or $R^3$ and $R^4$ are mutually linked to form an unsubstituted or substituted heterocyclic ring,
$R^5$ is an acyl radical,
n is an integer from 1 to 3, and
X is an alkylene, cyloalkylene, or arylene group.

and which, in combination with alkali-soluble binders, give positive-working mixtures which are used especially in recording materials for UV radiation and high-energy radiation. The materials are distinguished by a high resolution in conjunction with high image contrast and excellent storage stability.

19 Claims, No Drawings

OTHER PUBLICATIONS

"Hazen, Methoxonium Ions in Solvolysis. Neighboring Acetal Participation," *The Journal of Organic Chemistry*, vol. 35, No. 4, pp. 973-978 (Apr. 1970).

Fleming et al., "Protected 5-Hydroxypentanal Synthon." Chemical Abstracts, vol. 83, No. 21, Abstract No. 178949t (Nov. 1975).

Vig et al., "New Synthesis of 9-Keto-Trans-2-Decenoic Acid." Chemical Abstracts, vol. 83, No. 23, Abstract No. 192488y (Dec. 1975).

Agosta et al., "Loss of Water from Ketones in Isobutane Chemical Ionization Mass Spectrometry," *The Journal of Organic Chemistry*, vol. 41, No. 1, pp. 136-141 (Jan. 1976).

Vig et al., "Terpenoids. CIV. New Synthesis of Caparrapidiol.," Chemical Abstracts, vol. 84, No. 3, Abstract No. 17573w (Jan. 1976).

Gensler et al., "Synthesis of DL-Methyl Meromycolate," *The Journal of Organic Chemistry*, vol. 42, No. 1, pp. 118-125 (Jan. 1977).

Tsuji et al., "A Modified Synthesis of 2,15-Hexadecanedione, a Precursor of Muscone, from a Butadiene Telomer," Bulletin of the Chemical Society of Japan, vol. 51, No. 2, pp. 547-549 (Feb. 1978).

Belokon et al., "Synthesis of Crosslinked Polyacrylamide Gel Containing Salicylaldehye Fragments." Chemical Abstracts, vol. 89, No. 14, Abstract 110919b (Oct. 1978).

Sone et al., "1-(5-Oxohexyl)theobromine." Chemical Abstracts, vol. 91, No. 13, Abstract No. 108010w (Sep. 1979).

Anderson et al., "Synthesis of C-Ring-Functionalize A-Ring-Aromatic Trichothecane Analogues," *The Journal of Organic Chemistry*, vol. 45, No. 3, pp. 501-506 (Feb. 1980).

Tatsuta et al., "Stereospecific Total Synthesis and Absolute Configuration of a Macrocyclic Lactone Antibiotic, A26771B," Tetrahedron Letters, vol. 21, No. 15, pp. 1479-1482 (1980).

Kametani et al., "New Construction of a Steroidal Ring System. Stereoselective Synthesis of ()-Androstane-2,17-dione," *The Journal of Organic Chemistry*, vol. 48, No. 1, pp. 31-33 (Jan. 1983).

Creary et al., "Reaction of Triflates with Potassium Diethyl Phosphate. Formation of Phosphate Esters," *The Journal of Organic Chemistry*, vol. 48, No. 17, pp. 2887-2891 (Aug. 1983).

Joshi et al., "Convenient Synthetic Route to 6,8-Dioxabicyclo[3.2.1]octanes, the Aggregation Pheromone Components of Bark Beetles," *Journal of the Chemical Society*, Perkin Transactions 1 (1983).

Jaeger et al., "Destructible' Surfactants Based on a Ketal Group," *The Journal of Organic Chemistry*, vol. 49, No. 23, pp. 4325-4571 (Nov. 1984).

Balezina et al., "Insect Pheromones and their Analogs," Chemical Abstracts, vol. 102, No. 11, Abstract No. 95437j (Mar. 1985).

Stewart et al., "Preparation of $\alpha$-Arylsulfonyl Lactams," Chemical Abstracts, vol. 107, No. 11, Abstract No. 96539j (Sep. 1987).

Odinokov et al., "Ozonolysis of Alkenes and Reactions of Polyfunctional Compounds," *The Journal of Organic Chemistry of the USSR*, vol. 23, No. 11, Part 1 (Nov. 1987).

Allmendinger et al., "Aminofluoroalkenates as Peptide Mimetics," Chemical Abstracts, vol. 113, No. 17 Abstract No. 153046w (Oct. 1990).

Reichmanis et al., "Chemistry and Processes for Deep-UV Resists," *Microelectronic Engineering, vol. 13, pp. 3-10 (Mar. 1991)*.

Schlegel et al., "Highly Sensitive Positive Deep UV Resist Utilizing a Sulfonate Acid Generator and a Tetrahydropyranyl Inhibitor," *Microelectronic Engineering*, vol. 13, pp. 33-36 (Mar. 1991).

F. M. Houlihan et al., "An Evaluation of Nitrobenzyl Ester Chemistry for Chemical Amplification Resists", SPIE vol. 920, 1988, pp. 67-73.

C. C. Petropoulos, "Synthesis of Novel Photodegradable Poly($\alpha$-Nitrobenzaldehyde Acetal) Polymers", Journal of Polymer Science vol. 15, 1977, pp. 1637-1644.

C. G. Willson, "Organic Resist Materials-Theory and Chemistry", Introduction to Microlithography ACS Symp. Ser. 219, Mar. 20-25, 1983, pp. 88-159.

ACID-CLEAVABLE RADIATION-SENSITIVE COMPOUNDS, POSITIVE WORKING RADIATION-SENSITIVE MIXTURE CONTAINING THESES COMPOUNDS, AND RADIATION-SENSITIVE RECORDING MATERIAL PRODUCED WITH THIS MIXTURE

BACKGROUND OF THE INVENTION

1. Field of the Invention

The invention relates to radiation-sensitive and acid-cleavable compounds and to a radiation-sensitive mixture which is positive-working, i.e., which becomes soluble as a result of irradiation, and which contains these compounds. The mixture contains p1 (a) a binder which is insoluble in water and soluble or at least swellable in aqueous alkaline solutions, and (b) a compound which generates a strong acid under the action of actinic radiation and which has at least one acid-cleavable C—O—C bond.

The invention also relates to a radiation-sensitive recording material which has been produced from this mixture and which is suitable for producing photoresists, electronic components, printing plates or for chemical milling.

2. Description of Related Art

The continuing reduction in the size of the structures, for example in chip manufacture down into the range of less than 1 μm, requires modified lithographic techniques. To form images of such fine structures radiation of a short wavelength is used, such as high-energy UV light, electron beams and X-rays. The radiation-sensitive mixture must be adapted to the short-wave radiation. A compilation of the requirements to be met by the radiation-sensitive mixture is given in the article by C. G. Willson "Organic Resist Materials—Theory and Chemistry. [Introduction to Microlithography, Theory, Materials, and Processing, editors L. F. Thompson, C. G. Willson, M. J. Bowden, ACS Symp. Ser., 219, 87 (1983), American Chemical Society, Washington].

There is therefore an increased demand for radiation-sensitive mixtures which can be used in the more recent technologies, such as mid-UV or deep-UV lithography [exposure, for example, with excimer lasers at wavelengths of 305 nm (XeF), 248 nm (KrF), 193 nm (ArF)], electron beam lithography or X-ray lithography, and which, furthermore, are preferably sensitive in a wide spectral range and correspondingly can also be used in conventional UV lithography.

Positive-working radiation-sensitive mixtures for producing radiation-sensitive recording materials are known. For example, mixtures which contain o-quinone-diazide derivatives in binders soluble in aqueous alkaline media, for example novolaks or polyhydroxystyrenes, are commercially available. However, the sensitivity of these materials to actinic radiation, and especially to high-energy short-wave radiation, such as light from a KrF-excimer laser having a wavelength of 248 nm or electron beams, is inadequate.

Positive-working radiation-sensitive mixtures are also known in which an acid is generated by the action of actinic radiation on a photoinitiator contained in this mixture and this acid then, in a subsequent reaction, renders an acid-cleavable compound likewise contained in the mixture which is soluble in the irradiated areas under the action of an appropriate, preferably aqueous alkaline, developer. Such materials are in general distinguished by an enhanced sensitivity to actinic radiation.

Numerous mixtures are known which contain a polymeric binder soluble in aqueous alkaline solutions, a solubility-inhibiting compound and a compound which, on irradiation, generates the acid required for cleavage. The binder is in most cases a novolak resin. Many of these mixtures have a high sensitivity to actinic radiation. They are designated as chemically amplified, photocatalytic 3-component systems.

Of these mixtures, those whose acid-cleavable component contains one or more acetal units have especially gained commercial importance. These mixtures have, however, certain disadvantages. Particularly, they demonstrate only a limited stability on the substrate materials to which they have to be applied, and thus lead to unsatisfactory, not reducible reproduction of the image original. This can be improved only by introducing additional protective layers, for example, according to DE-A 3,621,376 equivalent to U.S. Pat. No. 4,840,867. The causes of the deterioration in the image reproduction are not known in detail and have not been adequately investigated. For example, the process window, i.e., the processing latitude, for the exposure of these mixtures is very narrow and frequently not unambiguously reproducible. In particular, the quality of the image reproduction greatly depends on the time difference between exposure and development, the so-called delay time. In principle, it must be assumed that diffusion processes which cause this behavior are not easily controllable. In addition, however, it may be presumed that during drying of the mixture on a substrate material partial vaporization of the photoinitiator or of the acid-unstable compound, or segregation of the individual mixture constituents, takes place. This is observed with particular frequency in the case of acid-unstable compounds having a low solubility in the usual coating solvents.

It is also known from the papers by C. C. Petropoulos [J. Polym. Sci., Polym. Chem. Ed., 15, 1637 (1977)] that aromatic acetals which carry a nitro group in the vicinal position, are photodecomposable by high-energy UV radiation without acid catalysis, and can be used in positive-working radiation-sensitive recording materials. The photosensitivity of these compounds is however inadequate for applications in practice, since their photoreaction cannot be chemically amplified.

In DE-A 3,721,741 equivalent to U.S. Pat. No. 4,883,740, radiation-sensitive mixtures are described which contain a polymeric binder insoluble in water and soluble in aqueous alkaline solutions, and an organic compound which contains at least one acid-cleavable grouping and a grouping which generates a strong acid under the action of radiation. The radiation-sensitive groups described are exclusively onium salt groups, in particular sulfonium salt groups.

The use of onium salts, such as diazonium, phosphonium, sulfonium and iodonium salts of non-nucleophilic acids such as $HSbF_6$, $HAsF_6$ or $HPF_6$ as photolytic acid generators involves disadvantages which drastically restrict their possible uses in various fields of application. For example, many of the onium salts are toxic. Their solubility is inadequate in many solvents, which is why only a few solvents are suitable for preparing a coating solution. Furthermore, when the onium salts are used, undesired foreign atoms are sometimes introduced which can cause interference with the process, especially in microlithography. Moreover, the onium salts form Brönstedt acids, which have a very severe corrosive action, in the photolysis. These acids attack sensitive substrates, so that the use of such mixtures leads to unsatisfactory results. Halogen compounds such as trichloromethyltriazine derivatives or trichloromethyloxadiazole derivatives also form hydrohalic acids which have a severely corrosive action.

In more recent papers by F. M. Houlihan et al., SPIE 920, 67 (1988), it was shown by reference to positive-working systems that, in addition to the above-mentioned acid generators, nitrobenzyl tosylates, which on exposure generate sulfonic acids having a low migration tendency, can be used in certain acid-unstable resist formulations. It can be deduced from these results that such compounds can also be used for photo-curable systems. However, the sensitivities thus achieved with these compounds, especially to UV radiation from 350 to 450 nm, and the thermal stability of the photoresists have proven to be inadequate.

There is thus a demand for radiation-sensitive mixtures which do not have the disadvantages described above and which possess a reactivity suitable in practice.

SUMMARY OF THE INVENTION

It is therefore an object of the invention to propose photolytically acid-generating and acid-cleavable compounds, and a radiation-sensitive mixture based thereon, where the photolytically acid-generating compound should be as stable as possible on all known substrates and which gives an acid as the photolysis product which does not have a corrosive action. Furthermore, the invention should provide a radiation-sensitive mixture which, in particular, avoids a segregation of the photoactive compound and of the solubility-differentiating compound.

It is a further object of the present invention to provide a recording material which gives a substantially defect-free positive image of the mask and high flank stability, and which is suitable for the production of photoresists, electronic components, and printed plates.

It is also an object of the present invention to provide a process for producing such a recording material.

It is a further object of the invention to provide a method for preparing an image pattern with the use of the recording material.

In accomplishing the foregoing objectives, there has been provided, in accordance with one aspect of the present invention, a compound of the formula I

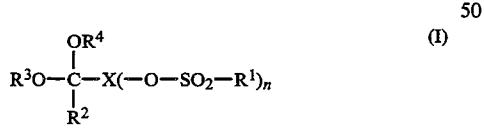

in which $R^1$ is an unsubstituted or substituted alkyl, fluorinated alkyl, perfluoroalkyl or aryl radical, $R^2$ is a hydrogen atom, an unsubstituted or substituted alkyl radical, or unsubstituted or substituted aryl radical, $(R^1-SO_2-O-)_nX-$, or $R^3O-$, $R^3$ and $R^4$ are identical or different and are unsubstituted or substituted alkyl, cycloalkylalkyl, cycloalkenylalkyl or aralkyl radicals, in which 1 to 3 aliphatic $CH_2$ or CH groups are optionally replaced by one or more of $NR^5$, O, S, CO, CO—O, CO—NH, O—CO—NH, CO—NH—CO, NH—CO—NH, $SO_2$, $SO_2$—O or $SO_2$—NH, or unsubstituted or substituted alkenyl, alkynyl, cycloalkyl or cycloalkenyl radicals, or $R^3$ and $R^4$ are mutually linked to form a heterocyclic ring, $R^5$ is an acyl radical, n is an integer from 1 to 3, and X is an alkylene, cyloalkylene, or arylene group if n is 1 or X is a(n+1)-valent radical of an alkane, cycloalkane, or arene if n is 2 or 3.

If n is 2 or 3, the radicals $R^1$ may be the same or different.

There has also been provided a positive-working radiation-sensitive mixture which comprises a. at least one binder which is insoluble in water and soluble or at least swellable in aqueous alkaline solutions, and b. at least one compound of the formula I, which generates a strong acid under the action of actinic radiation and which has at least one acid-cleavable C—O—C bond.

There has further been provided a positive-working radiation-sensitive recording material comprising a support and a radiation-sensitive layer, wherein the layer comprises a radiation-curable mixture as described above.

There has also been provided a method of producing such a recording material which comprises dissolving the radiation-sensitive mixture in a solvent, applying the resulting solution to the support, and removing the solvent.

There has further been provided a method of preparing an image pattern which comprises irradiating the radiation-sensitive layer imagewise, optionally heating the layer, treating the layer with a developer which removes the irradiated areas of the layer, and optionally post-hardening the developed layer structures.

Further objects, features, and advantages of the present invention will become apparent from the detailed description of preferred embodiments that follows.

DETAILED DESCRIPTION OF THE PREFERRED EMBODIMENTS

Any compound within the scope of formula I is within the scope of the presention invention. Those compounds of the formula I are preferred in which $R^1$ is an alkyl radical which has 1 to 6 carbon atoms and may be highly fluorinated, i.e. in which at least 50% of the hydrogen atoms are replaced by fluorine atoms, or an aryl radical which has 6 to 12 carbon atoms and $R^2$ is a hydrogen atom or an $R^3O$ radical.

$R^3$ and $R^4$ are preferably identical and especially are alkyl, cycloalkylalkyl, cycloalkenylalkyl or aralkyl groups having less than 16 carbon atoms, it being possible for 1 to 3 aliphatic $CH_2$ or CH groups to be replaced by $NR^5$, O, S, CO, COO, CONH, OCONH, CONHCO, NHCONH, $SO_2$, $SO_2O$ or $SO_2NH$, or alkenyl, alkynyl, cycloalkyl or cycloalkenyl radicals. If $R^3$ and $R^4$ together form a heterocyclic ring, this is preferably a 1,3-dioxolane or 1,3-dioxane ring.

$R^5$ can especially be an alkanoyl or aroyl, an alkyl-, alkenyl-, analkyl- or aryl-sulfonyl or an alkyl-, alkenyl-, aralkyl- or aryl-phosphonyl radical having up to 12 carbon atoms, particularly preferably an alkanoyl radical having 2 to 6 carbon atoms or an aroyl radical having 7 to 10 carbon atoms.

X preferably is an alkylene group having 2 to 10 carbon atoms, a cycloalkylene group having 4 to 10 carbon atoms or an arylene group having 6 to 12 carbon atoms, each substituted by 1 to 3 sulfonyloxy groups $R^1$—$SO_2$—O—.

Within the scope of the present invention, the aryl or arylene groups can be groups which are either unsubstituted or substituted by any suitable substituents, including halogen atoms or alkyl, fluorinated alkyl, alkoxy, nitro or cyano groups. Aralkyl groups are understood to be those which contain 1 to 2 aromatic radicals linked through aliphatic groupings and bound via an aliphatic carbon atom.

Those compounds of the formula I are particularly preferred in which $R^1$ is a methyl, ethyl, trifluoromethyl or hexafluoroisopropyl radical or a phenyl radical which may be substituted by 1 to 3 alkyl or alkoxy groups having 1 to 3 carbon atoms, 1 to 3 halogen atoms, 1 or 2 nitro, cyano or trifluoromethyl groups or appropriate combinations thereof and X is an arylene group which is substituted by 1 to 3 sulfonyloxy groups $R^1$—$SO_2$—O—.

Those compounds of the formula I are very particularly preferred in which $R^2$ is a hydrogen atom and X is an aromatic six-membered ring substituted by 1 to 3 sulfonyloxy groups $R^1$—$SO_2$—O.

The compounds can be prepared in any suitable manner. This can be carried out, for example, analogously to the synthesis instructions given in EP-A 0,312,757, which is hereby incorporated by reference, where the appropriate sulfonic acid ester derivative must be prepared in a preceding stage. Further suitable synthesis instructions are to be found in DE-A 2,610,842, depending on the nature of the substituents $R^2$, $R^3$ and $R^4$. The synthesis of typical and preferred representatives of these classes of compounds is described below by reference to individual examples.

PREPARATION EXAMPLE 1

1st stage: 80.6 g (0.66 mol) of 4-hydroxybenzaldehyde were dissolved in 200 ml of tetrahydrofuran, 138 ml of triethylamine were added and the mixture was cooled to −5° C. 125.8 g (0.66 mol) of p-toluenesulfonic acid chloride, dissolved in 330 ml of tetrahydrofuran and precooled to −5° C., were added dropwise to the above mixture at −8° to −5° C. Stirring was continued for 1 hour at room temperature. The solution was poured into 1,000 ml of distilled water, and the mixture was adjusted to pH 2 with concentrated hydrochloric acid. The oil which precipitated was taken up in ether, and the aqueous phase was extracted with ether. The combined organic phases were washed with water and dried. After concentrating, a residue remained which was recrystallized from cyclohexane/methylene chloride. This gave 120 g (66.1%) of 4-(toluene-4-sulfonyloxy)-benzaldehyde (a white solid having a melting point of 70° to 72° C.).

2nd stage: 7.2 g (0.026 mol) of 4-(toluene-4-sulfonyloxy)-benzaldehyde were heated under reflux together with 7.2 g (0.052 mol) of phenoxyethanol, 4.25 g (0.0286 mol) of triethyl orthoformate and 100 mg of p-toluenesulfonic acid in 150 ml of toluene. After about 2 hours, a part of the distillate was taken off until the top temperature corresponded to the boiling point of pure toluene. This procedure was repeated until the top temperature no longer fell below the boiling point of pure toluene. After a further 2 hours, the distillation was assisted for about 45 minutes by applying a vacuum of 4 mm Hg, and all volatile constituents were distilled off. The residue was cooled and taken up in methylene chloride, washed twice with 2% sodium hydroxide solution and deionized water each time, and the organic phase was dried. After removal of the solvent, 12.9 g (93%) of a pale yellow oil remained, which proved to be the desired 4-(toluene-4-sulfonyloxy)benzaldehyde bis(2-phenoxyethyl)acetal (compound No. 1 shown below).

$C_{30}H_{30}O_7S$ calc.: C 67.40 H 5.66 S 6.00 [534.62]
found: C 67.7 H 5.7 S 5.9

PREPARATION EXAMPLE 2

1st stage: 80.6 g (0.66 mol) of 4-hydroxybenzaldehyde were dissolved in 200 ml of tetrahydrofuran, 138 ml of triethylamine were added and the mixture was cooled to −5° C. 75.3 g (0.66 mol) of methanesulfonic acid chloride, dissolved in 330 ml of tetrahydrofuran and precooled to −5° C., were added dropwise to the above mixture at −8° to −5° C. Stirring was continued for 1 hour at room temperature. The solution was poured into 1,000 ml of distilled water, and the mixture was adjusted to pH 2 with concentrated hydrochloric acid. The oil which precipitated was taken up in ether, and the aqueous phase was extracted with ether. The combined organic phases were washed with water and dried. After concentrating, an oil remained which was recrystallized from cyclohexane. This gave 84 g (63.7%) of 4-methanesulfonyloxybenzaldehyde (a white solid having a melting point of 61° to 63° C.).

2nd stage: 5.2 g (0.026 mol) of 4-methanesulfonyloxybenzaldehyde were heated in an oil bath to 130° C. together with 7.6 g (0.052 mol) of a urethane alcohol prepared by condensing 1 mol of ethylene carbonate with 1 mol of n-propylamine, 4.25 g (0.0286 mol) of triethyl orthoformate and 100 mg of p-toluenesulfonic acid. In this process a highly mobile liquid distilled off. After 2 hours, the distillation was assisted for about 45 minutes by applying a vacuum of 1 mm Hg. The residue was cooled and was taken up in methylene chloride, washed twice with 2% sodium hydroxide solution and deionized water each time, and the organic phase was dried. After removal of the solvent, 11.7 g (93%) of 4-methanesulfonyloxybenzaldehyde bis[2-(N-propylcarbamoyloxy)ethyl]acetal (an amber-colored melt; Compound No. 2 below) remained. The compound shows a single $^1$H-NMR signal for the acetal group at 5.65 ppm.

PREPARATION EXAMPLE 3

1st stage: 8.29 g (0.06 mol) of 3,4-dihydroxybenzaldehyde were dissolved in 40 ml of tetrahydrofuran, 18.5 ml of triethylamine were added, and the mixture cooled to −5° C. 22.9 g (0.12 mol) of p-toluenesulfonic acid chloride, dissolved in 80 ml of tetrahydrofuran and precooled to −5° C., were added thereto dropwise at −8° to −5° C. Stirring was continued for 2 hours at room temperature. The solution was poured into 1,000 ml of distilled water, and the mixture was adjusted to pH 2 with concentrated hydrochloric acid. The oil which precipitated solidified after prolonged stirring to give a brown crystal paste. The crude product was filtered off with suction and dried. It was recrystallized from cyclohexane/methylene chloride with the addition of active charcoal. This gave 15.9 g (59.4%) of 3,4-bis-(toluene-4-sulfonyloxy)-benzaldehyde (white solid having a melting point of 95° to 97° C.).

2nd stage: 11.6 g (0.026 mol) of 3,4-bis-(toluene-4-sulfonyloxy)-benzaldehyde were heated in an oil bath at 130° C. together with 7.44 g (0.052 mol) of N-(2-hydroxyethyl) succinimide, 4.25 g (0.0286 mol) of triethyl orthoformate and 100 mg of p-toluenesulfonic acid. In this process a highly mobile liquid distilled off. After 2 hours, the distillation was assisted for about 45 minutes by applying a vacuum of 1 mm Hg. The residue was cooled and was taken up in methylene chloride, washed twice with 2% sodium hydroxide solution and deionized water each time, and the organic phase was dried. After removal of the solvent, 16.9 g of an amber-colored melt remained, which was recrystallized from ethanol. This gave 12.8 g (90.6%) of 3,4-bis-(toluene-4-sulfonyloxy)benzaldehydebis-(2-succinimidoethyl)-acetal (white crystals having a melting point of 127° to 128° C.; Compound No. 3 below).

$C_{33}H_{33}N_2O_{12}S_2$ calc.: C 55.54 H 4.66 N 3.92 S 8.98 [713.70] found: C 55.9 H 4.5 N 4.0 S 9.0

PREPARATION EXAMPLE 4

1st stage: 15.4 g (0.1 mol) of 3,4,5-trihydroxybenzaldehyde were dissolved in 40 ml of tetrahydrofuran, 45.5 ml of triethylamine were added, and the mixture was cooled to −5° C. 57.2 (0.3 mol) of p-toluenesulfonyl chloride, dissolved in 80 ml of tetrahydrofuran and precooled to −5° C., were added dropwise thereto at −8° to −5° C. Stirring was continued for 2 hours at room temperature. The solution was poured into 1000 ml of distilled water, and the mixture was adjusted to pH 2 with concentrated hydrochloric acid. The oil which had precipitated solidified after prolonged stirring to give a brown crystal paste. The crude product was filtered off with suction and dried. It was recrystallized from ethyl acetate with addition of active charcoal. This gave 46.8 g (75.9%) of 3,4,5-tris-(toluene-4-sulfonyloxy)benzaldehyde (white solid of melting point 159° C.).

2nd stage: 18.5 g (0.03 mol) of 3,4,5-tris-(toluene-4-sulfonyloxy)-benzaldehyde were stirred at room temperature together with 5.2 g (0.035 mol) of triethyl orthoformate and 100 mg of p-toluenesulfonic acid in 150 ml of toluene. A slight evolution of heat was observed. The mixture was left to stand overnight. 8.84 g (0.065 mol) of 3-phenylpropanol and a further 100 mg of p-toluenesulfonic acid were added, followed by heating under reflux. The remaining procedure followed is found in Preparation Example 1. The residue was cooled and taken up in methylenechloride, washed twice with 2% sodium hydroxide solution and deionized water each time, and the organic phase was dried. After removal of the solvent, 21.4 g (82%) of a honey-colored melt remained, which could not be made to crystallize. A thin-layer chromatogram (DC) showed that the desired 3,4,5-tris-(toluene-4-sulfonyloxy)-benzaldehyde bis-(3-phenylpropyl)-acetal (Compound No. 4 below) was more than 92% pure.

$C_{46}H_{46}O_{11}S_3$ calc. C 63.39 H 5.39 S 11.03 [871.58] found C 65.0 H 5.4 S 10.7

Further examples of compounds according to the invention are listed below. These were synthesized analogously to processes known from the literature. Their authenticity was confirmed by elemental analysis and $^1$H-NMR.

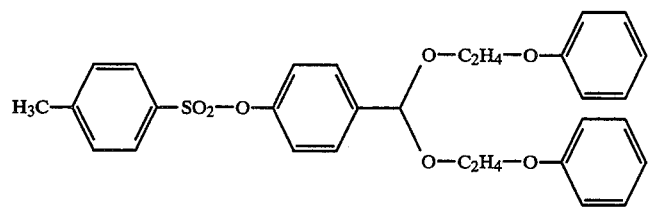

Compound No. 1:

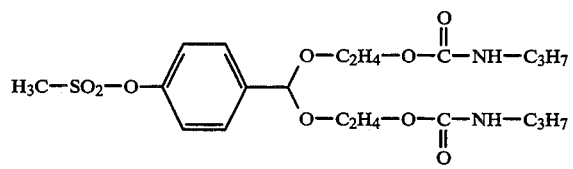

Compound No. 2:

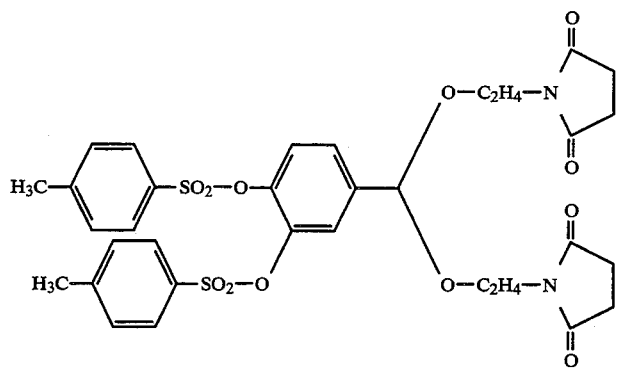

Compound No. 3:

-continued
Compound No. 4:
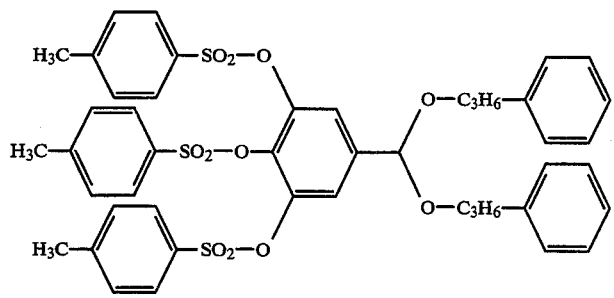
Compound No. 5:
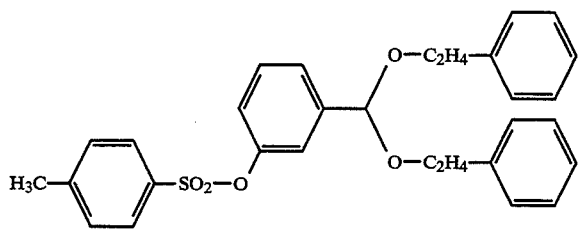
Compound No. 6:
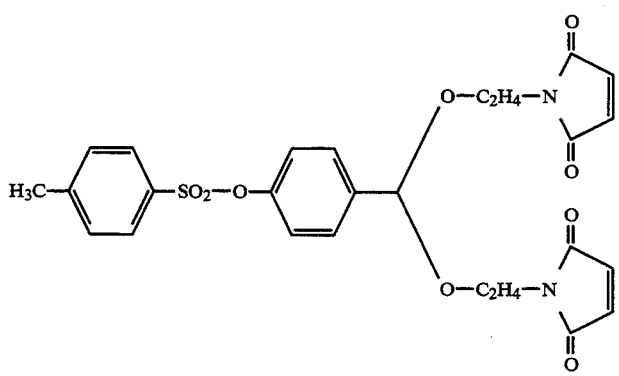
Compound No. 7:
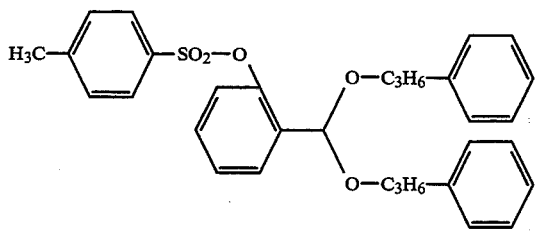
Compound No. 8:
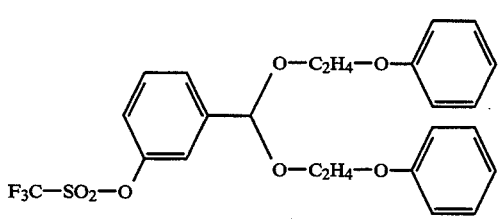
Compound No. 9:
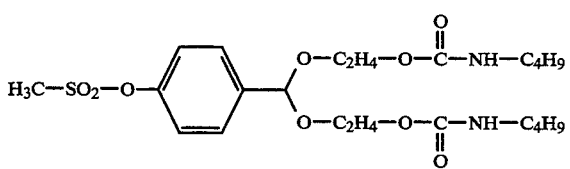

-continued
Compound No. 10:
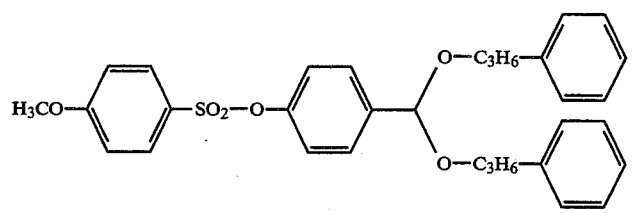
Compound No. 11:
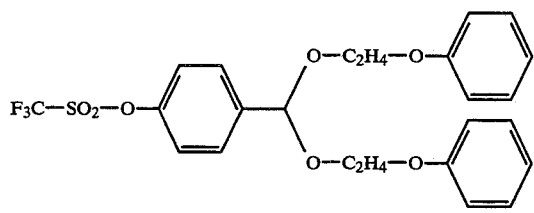
Compound No. 12:
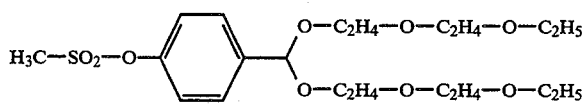
Compound No. 13:
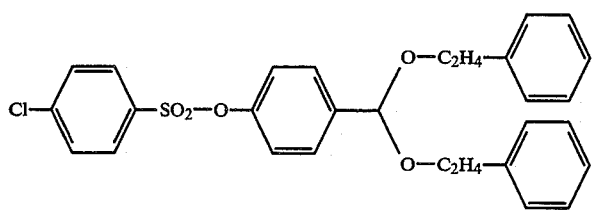
Compound No. 14:
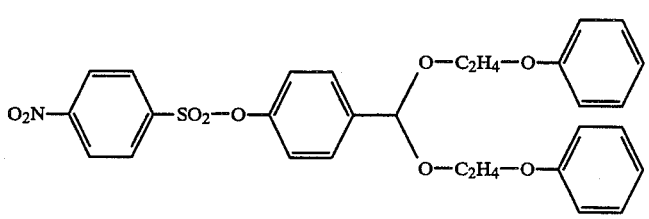
Compound No. 15:
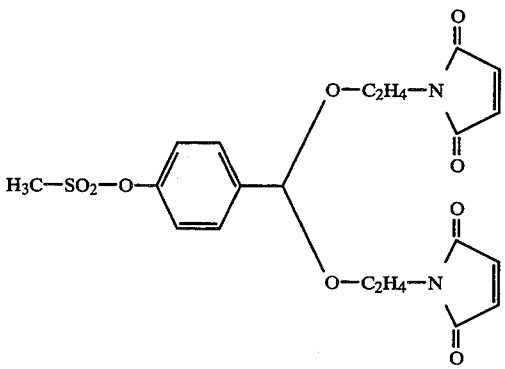
Compound No. 16:
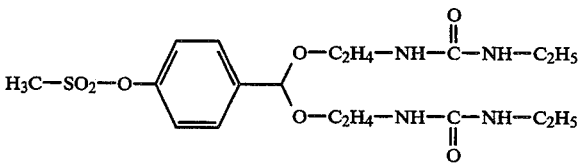

-continued
Compound No. 17:
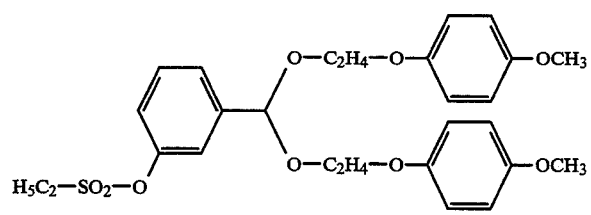
Compound No. 18:
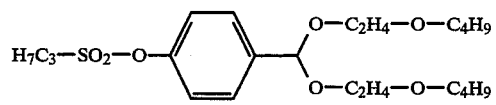
Compound No. 19:
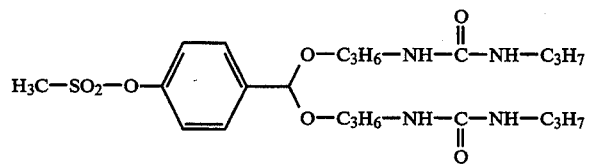
Compound No. 20:
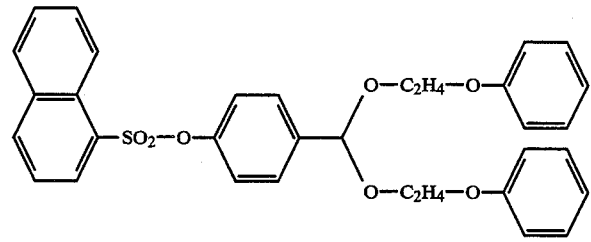
Compound No. 21:
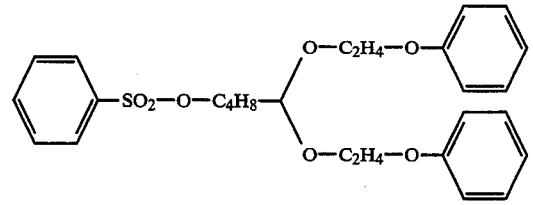
Compound No. 22:
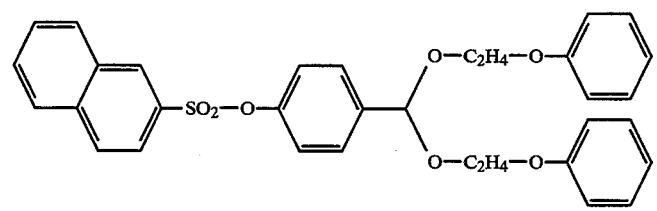
Compound No. 23:
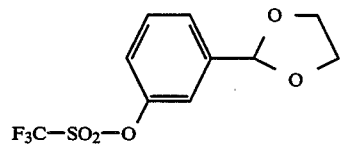
Compound No. 24:
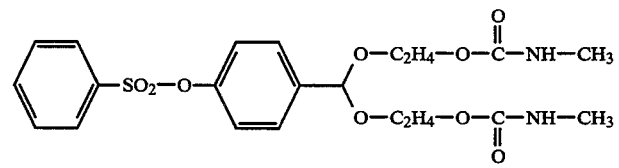

-continued
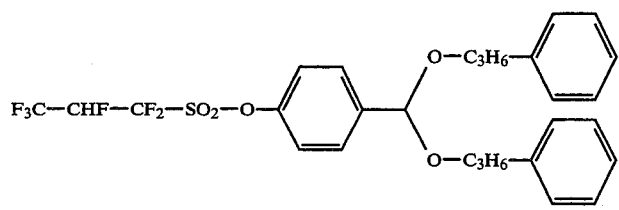
Compound No. 25:
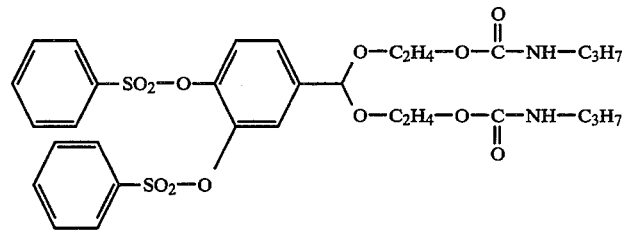
Compound No. 26:
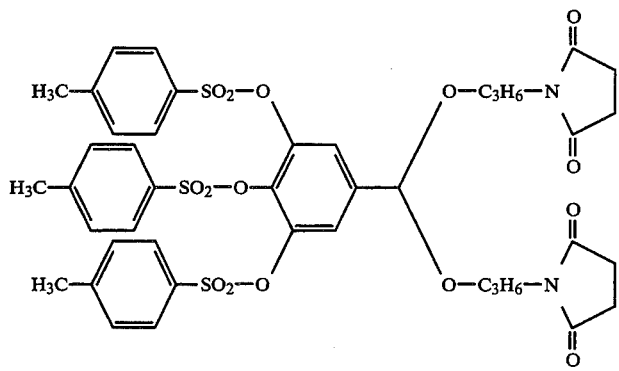
Compound No. 27:
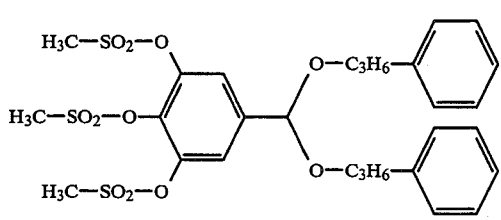
Compound No. 28:
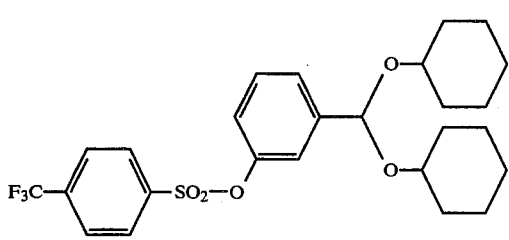
Compound No. 29:
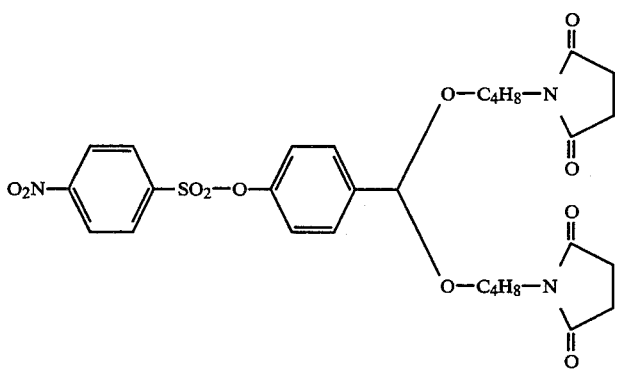
Compound No. 30:

-continued
Compound No. 31:
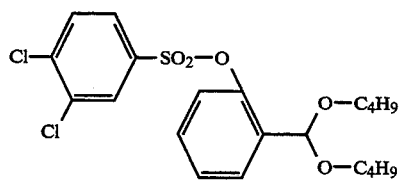
Compound No. 32:
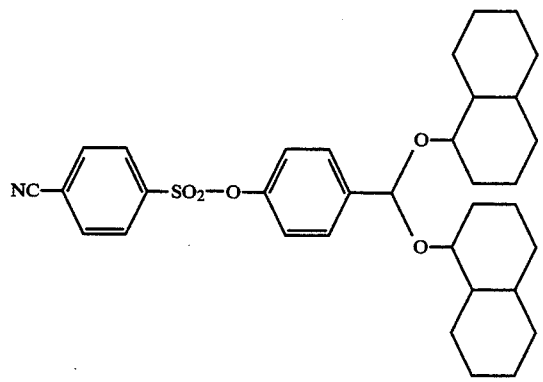
Compound No. 33:
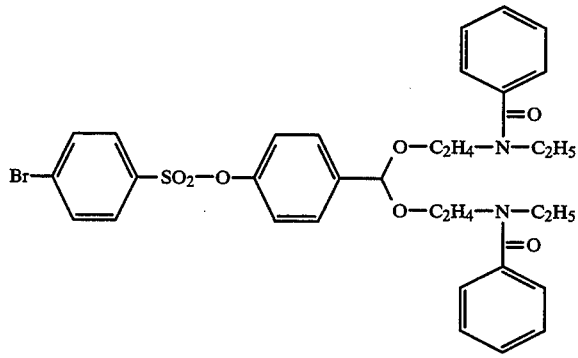
Compound No. 34:
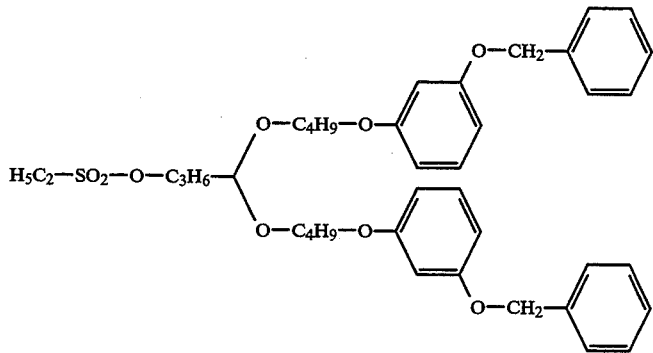
Compound No. 35:
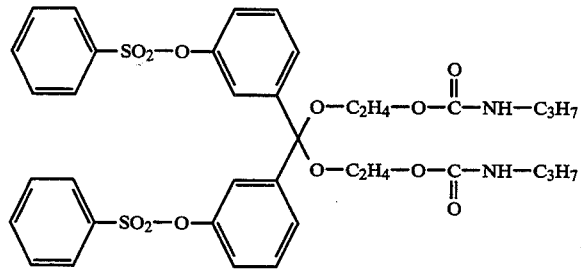

-continued
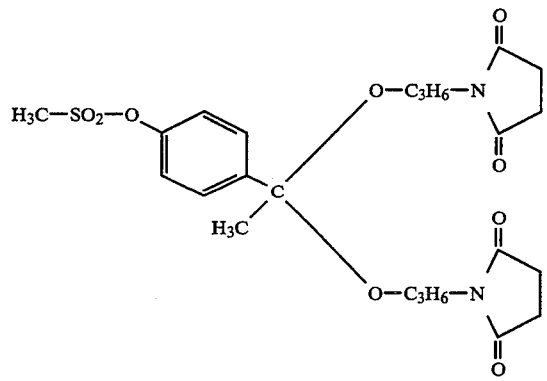
Compound No. 36:
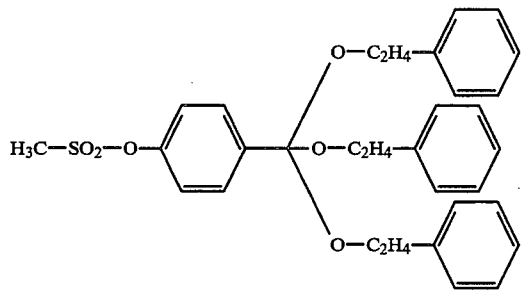
Compound No. 37:
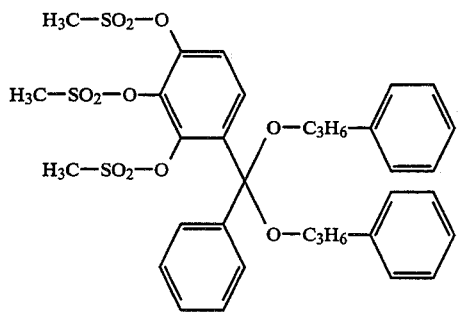
Compound No. 38:
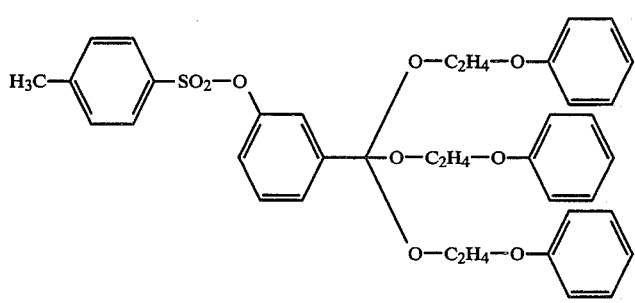
Compound No. 39:
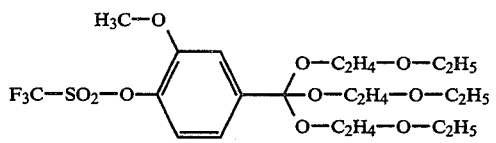
Compound No. 40:
Compound No. 41:
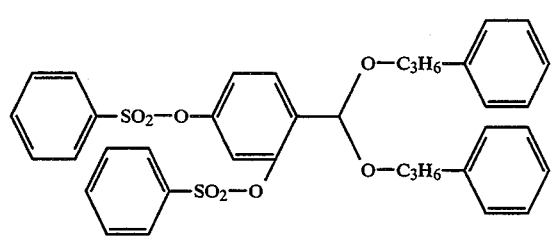

-continued
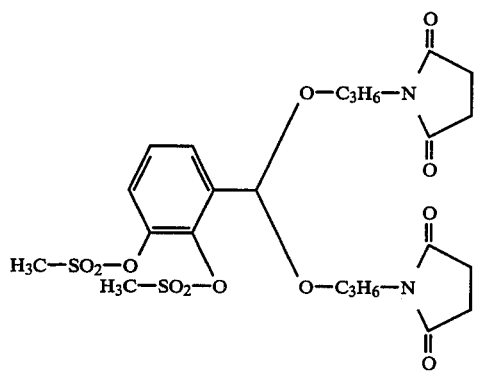
Compound No. 42:
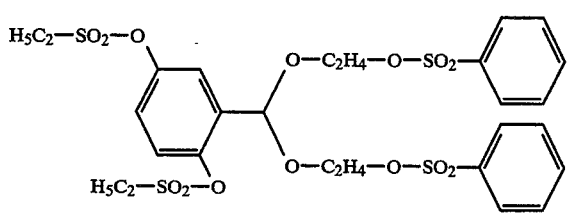
Compound No. 43:
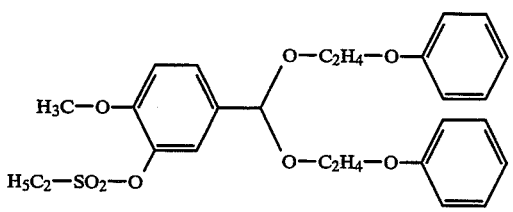
Compound No. 44:
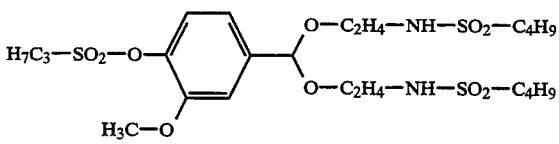
Compound No. 45:
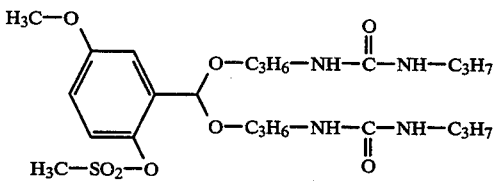
Compound No. 46:
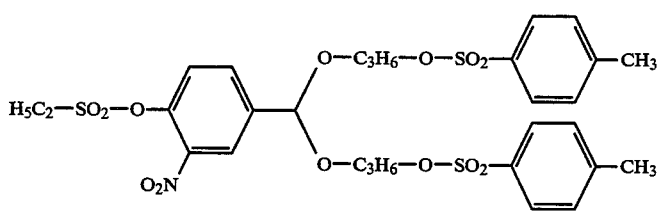
Compound No. 47:
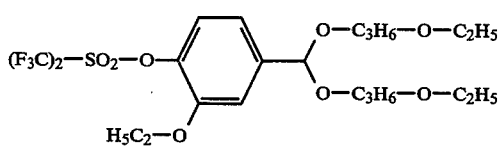
Compound No. 48:

Compound No. 49:

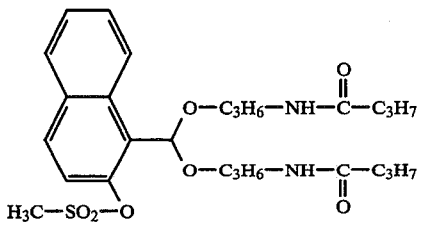

Those compounds which have acetal structures are particularly preferred. This is due to the fact that they are very readily accessible and are also extremely stable to hydrolysis both in solution and in layers, and that thus a stable recording material containing these compounds can be produced. As described in the Preparation Examples, the acetals according to the invention are based on certain aldehydes, of which the following are particularly preferred as starting compounds: 2-, 3- and 4-hydroxybenzaldehyde; 2,3-, 2,4-, 2,5- and 3,4-dihydroxybenzaldehyde; 2,3,4- and 3,4,5-trihydroxybenzaldehyde; 4-hydroxy-3-methylbenzaldehyde, 2-hydroxy-4-, 2-hydroxy-5-, 3-hydroxy-4-, and 4-hydroxy-3-methoxybenzaldehyde; 3,5-dimethyl-4-, 3,4-dimethoxy-5-, and 3-ethoxy-4-hydroxy-benzaldehyde; 2-hydroxy-5-, 3-hydroxy-4-, 4-hydroxy-3-, and 5-hydroxy-2-nitrobenzaldehyde; and 2-hydroxynaphthalene-1-carbaldehyde.

These aldehydes are commercially available, while other hydroxyaldehydes suitable according to the invention as precursors can, in general, be prepared in a simple manner by the most diverse methods. A review of these is given in Houben-Weyl, Methoden der organischen Chemie [Methods of Organic Chemistry], vol. 7/1.

According to the invention, a positive-working radiation-sensitive mixture is also provided which contains,
a) a binder which is insoluble in water and soluble or at least swellable in aqueous alkaline solutions and
b) a compound which generates a strong acid under the action of actinic radiation and which has at least one acid-cleavable C—O—C bond,
wherein the compound (b) comprises a compound of the formula I described above.

The radiation-sensitive mixtures according to the invention, obtained with the use of compounds of the formula I, are distinguished by high sensitivities over a wide spectral range. They are very particularly suitable for irradiation with high-energy UV radiation, preferably with light of a wavelength from 190 to 350 nm. They show high thermal stability and make it possible to accurately reproduce even superfine structures of an original. No corrosive photolysis products are generated by the exposure, so that the mixture can also be used on sensitive substrate materials.

The acid-cleavable photolytic acid generators contained in the radiation-sensitive mixture according to the invention can be used singly or in combination with other acid-unstable acid generators of the class according to the invention falling within Formula I. Furthermore, combinations with any other known photolytic acid generators are also possible. Even the onium salts mentioned at the outset, halogen compounds, especially trichloromethyltriazine derivatives or trichloromethyloxadiazole derivatives, o-quinonediazidesulfochlorides or organometal/organohalogen combinations are suitable. Overall, however, such combinations are not preferred since the disadvantages already mentioned in connection with known acid generators can under certain circumstances reappear in such radiation-sensitive mixtures.

The content of acid-unstable acid generators of the formula I in the mixture according to the invention can be varied depending on the intended use of the mixture and is in general between 2 and 60% by weight, preferably 5 to 50% by weight and particularly preferably 10 to 40% by weight, each relative to the total weight of solids in the layer.

If desired, other acid-cleavable compounds known in the art can be added to the mixtures according to the invention. The following compound classes are examples of classes which have proven suitable:

(1) compounds having at least one orthocarboxylic acid ester grouping and/or carboxylic acid amide-acetal grouping, the compounds also having a polymeric character and it being possible for the said groupings to occur as linking elements in the main chain or as substituents in side chains (see DE-A 2,610,842 and 2,928,636), (2) oligomeric or polymeric compounds with recurring acetal and/or ketal groupings in the main chain (see DE-A 2,306,248 and 2,718,254), (3) compounds having at least one enol ether grouping or N-acyliminocarbonate grouping (see EP-A 0,006,626 and 0,006,627), (4) cyclic acetals or ketals of β-ketoesters or β-ketoamides (see EP-A 0,202,196), (5) compounds having silyl ether groupings (see DE-A 3,544,165 and 3,601,264), (6) compounds having silylenol ether groupings (see DE-A 3,730,785 and 3,730,783), (7) monoacetals and monoketals, whose aldehyde or keto component respectively has a solubility of between 0.1 and 100 g/l in the developer (see DE-A 3,730,787), (8) ethers based on tertiary alcohols (see U.S. Pat. No. 4,603,101) and (9) carboxylic acid esters and carbonates of tertiary alcohols, allylic alcohols or benzylic alcohols [see U.S. Pat. No. 4,491,628 and J. M. Fréchet et al., J. Imaging Sci. 30, 59–64 (1986)].

Mixtures of the said acid-cleavable compounds can also be used. However, acid-cleavable compounds are preferably used which are classified under one of the above-mentioned types (1) to (9) and, amongst these, especially those which have an acid-cleavable C—O—C bond. Amongst these, those compounds are particularly preferred which belong to the types (1), (2), (7) and (9). Under type (2), especially the polymeric acetals are preferred, and, of the acid-cleavable compounds of type (7), especially those whose aldehyde or ketone component has a boiling point above 150° C., preferably above 200° C., are preferred. Overall, however, mixtures of such compounds are not preferred.

The compound (b) or the combination of compounds (b) is preferably present in a concentration from 2 to 60% by weight of the solids in the mixture.

The radiation-sensitive mixture according to the invention also contains at least one polymeric binder which is insoluble in water but soluble or at least swellable in aqueous alkaline solutions. Any known binder or mixture of binders meeting these conditions can be used. The binder is distinguished, in particular, by being compatible with the other constituents of the radiation-sensitive mixture according to the invention and having the lowest possible characteristic absorption, i.e., high transparency, especially in the wavelength range from 190 to 300 nm. Binders based solely on novolak condensation resins, which are generally used in combination with naphthoquinonediazides as the photoactive components, do not meet this requirement. Although novolak condensation resins show, after imagewise exposure, an increase in the solubility in aqueous alkaline developers in the exposed areas, their characteristic absorption is undesirably high in the region of the short wavelength desired for the irradiation.

Novalak condensation resins can, however, be used in a mixture with other resins of higher transparency. The mixing ratios here depend predominantly on the nature of the binder to be mixed with the novolak resin. Especially important factors are the degree of characteristic absorption of the binder in the said wavelength range, and also the miscibility with the other constituents of the radiation-sensitive mixture. In general, however, the binder of the radiation-sensitive mixture according to the invention should contain at most 30% by weight, especially at most 20% by weight, of a novolak condensation resin.

Suitable binders include homopolymers or copolymers of p-hydroxystyrene and homo and copolymers of alkyl derivatives thereof, for example of 3-methyl-4-hydroxystyrene, of 3,5-dimethyl-4-hydroxystyrene or 2,3-dimethyl-4-hydroxystyrene, and homopolymers or copolymers of other vinylphenols, for example of 2- or 3-hydroxystyrene or of 4-methyl-3-hydroxystyrene, or the esters or amides of (meth)acrylic acid with phenols, for example pyrocatechol, resorcinol, hydroquinone, pyrogallol or aminophenols and the corresponding amides with aromatic amines. Polymerizable compounds such as styrene, methyl methacrylate, methyl acrylate or the like can be used as comonomers.

Mixtures having an increased plasma resistance are obtained when silicon-containing vinyl monomers, for example vinyltrimethylsilane or allyltrimethylsilane, are used for the preparation of copolymers of the above type. The transparency of these binders is generally higher in the region of interest, so that improved structuring is possible.

Homopolymers or copolymers of maleimide can also be used with equally good results. These binders too show a high transparency in the wavelength range described. Here again, the comonomers preferably used are styrene, substituted styrenes, vinylphenols, vinyl ethers, vinyl esters, vinylsilyl compounds or (meth)acrylates.

Copolymers of styrene can also be used with comonomers which effect an increase in solubility in aqueous alkaline solutions. These include, for example, maleic anhydride, maleic acid half-esters or the like.

The said binders can also be mixed with one another if this does not impair the optical quality of the radiation-sensitive mixture. However, binder mixtures are not preferred.

Any amount of binder can be used depending on the intended use of the mixture. The quantity of binder is in general 40 to 98% by weight, especially 50 to 95% by weight, preferably 60 to 90% by weight, relative to the total weight of solids in the radiation-sensitive mixture.

The extinction of the binder or of the combination of binders (a) in the wavelength range of the sensitivity of compound (b) is preferably less than 0.5 $\mu m^{-1}$.

If appropriate, one or more of dyes, pigments, plasticizers, wetting agents and flow agents, polyglycols and cellulose ethers, for example ethylcellulose, can be added to the radiation-sensitive mixtures according to the invention to improve special requirements, such as flexibility, adhesion and gloss.

Any known substrate can be coated with the radiation sensitive mixture of the invention in any known manner. When such a substrate is to be coated, the radiation-sensitive mixture is expediently dissolved in a solvent or in a combination of solvents. Ethylene glycol, ethylene glycol monomethyl ether, ethylene glycol dimethyl ether, ethylene glycol monoethyl ether or propylene glycol monoalkyl ethers, especially propylene glycol methyl ether, aliphatic esters (for example ethyl acetate, hydroxyethyl acetate, alkoxyethyl acetate, n-butyl acetate, propylene glycol alkyl etheracetate, especially propylene glycol methyl ether-acetate or amyl acetate), ethers (for example dioxane), ketones (for example methyl ethyl ketone, methyl isobutyl ketone, cyclopentanone and cyclohexanone), dimethylformamide, dimethylacetamide, hexamethylphosphoramide, N-methylpyrrolidone, butyrolactone, tetrahydrofuran and mixtures thereof are particularly suitable for this purpose. Glycol ethers, aliphatic esters and ketones are particularly preferred.

Ultimately, the choice of the solvents depends on the coating process used, the desired layer thickness and the drying conditions. The solvents must also be chemically neutral, i.e., they must not react irreversibly with the other layer components.

The solution prepared with the said solvents generally has a solids content from 5 to 60% by weight, preferably up to 50% by weight.

The invention also relates to a radiation-sensitive recording material which is comprised essentially of a substrate and, preferably located thereon, a radiation-sensitive layer of the radiation-sensitive mixture according to the invention.

Possible substrates are all those materials of which capacitors, semiconductors, multi-layer printed circuits or integrated circuits are composed, or from which these can be produced. Silicon substrates which can also be thermally oxidized and/or coated with aluminum and also doped merit special mention. In addition, all other substrates usual in semiconductor technology can be used, such as silicon nitride, gallium arsenide and indium phosphide. Moreover, the substrates known from liquid crystal display manufacture are possible, such as, for example, glass and indium-tin oxide and also metal plates and foils, for example foils of aluminum, copper and zinc, bimetal foils and trimetal foils, and also electrically non-conductive foils on which metals have been vapor-deposited, and paper. These substrates can be thermally pretreated, superficially roughened, incipiently etched or pretreated with chemicals to improve desired properties, for example, to enhance the hydrophilic character.

To impart better cohesion and/or better adhesion of the radiation-sensitive layer to the substrate surface, the layer can contain an adhesion promoter. In the case of silicon or silica substrates, adhesion promoters of the aminosilane type such as, for example, 3-aminopropyltriethoxysilane or hexamethyldisilazane, can be used for this purpose. Also, a layer containing an adhesion promoter can be coated on the substrate, prior to applying the radiation-sensitive mixture.

Suitable supports for the production of photomechanical recording layers, such as printing forms for letterpress printing, planographic printing, screen printing and flexographic printing, are, in particular, aluminum plates, which may have been anodically oxidized, grained and/or silicated beforehand, zinc and steel plates which may be chromium-plated, and also plastic films and paper.

The recording material according to the invention is exposed imagewise to actinic radiation. Suitable radiation sources are especially metal halide lamps, carbon arc lamps, xenon lamps and mercury vapor lamps. Likewise, exposure can be carried out with high-energy radiation such as laser radiation, electron beams or X-rays. However, lamps which can emit light of a wavelength from 190 to 260 nm, i.e., especially xenon lamps and mercury vapor lamps, are particularly preferred. Furthermore, laser light sources can also be used, for example excimer lasers, especially KrF or ArF lasers, which emit at 248 and 193 nm respectively. The radiation sources must show adequate emission in the said wavelength ranges.

The thickness of the light-sensitive layer depends on the intended use. In general it is between 0.1 and 100 $\mu$m, preferably between 1.0 and 10 $\mu$m.

The invention also relates to a process for producing a radiation-sensitive recording material. The radiation-sensitive mixture can be applied to the substrate by any known process, including spraying, flow-coating, rolling, whirler-coating and dip-coating. The solvent is then removed by evaporation, so that the radiation-sensitive layer remains on the surface of the substrate. The removal of the solvent can be promoted by heating the layer to temperatures of up to 150° C. The mixture can, however, also be first applied in the above-mentioned way to a temporary support, from which it is transferred under pressure and at an elevated temperature to the final support material. The materials used as temporary support can in principle be all those which are also suitable as support materials. Subsequently, the layer is irradiated imagewise and heated to improve the cleavage reaction. The layer is then treated with a developer solution which dissolves and removes the irradiated areas of the layer, so that an image of the original used in the imagewise irradiation remains on the substrate surface.

Any developer known in the art can be used. Suitable developers are especially aqueous solutions which contain silicates, metasilicates, hydroxides, hydrogen phosphates and dihydrogen phosphates, carbonates or hydrogen carbonates of alkali metal ions, alkaline earth metal ions and/or ammonium ions, and also ammonia and the like. Metal ion-free developers are described in U.S. Pat. No. 4,729,941, EP-A 0,062,733, U.S. Pat. Nos. 4,628,023, 4,141,733, EP-A 0,097,282 and EP-A 0,023,758. The content of these substances in the developer solution is in general 0.1 to 15% by weight, preferably 0.5 to 5% by weight, relative to the weight of the developer solution. Preferably, metal ion-free developers are used. Small quantities of a wetting agent can be added to the developers in order to facilitate the detachment of the soluble areas of the layer.

The developed layer structures can be post-hardened. This is effected in any known manner in general by heating on a hot plate up to a temperature below the flow temperature and subsequently exposing the whole area to the UV light from a xenon-mercury vapor lamp (range from 200 to 250 nm). As a result of the post-hardening, the image structures are crosslinked, so that in general they have a flow resistance up to temperatures of more than 200° C. The post-hardening can also be effected without a temperature increase solely by irradiation with high-energy UV light.

The radiation-sensitive mixture according to the invention may be used in the production of integrated circuits or of discrete electronic components by lithographic processes because they have a high light sensitivity, particularly on irradiation with light of a wavelength of between 190 and 300 nm. Since the mixtures bleach very well on exposure, finer structures can be achieved than is possible with the known mixtures. The developed resist layer here serves as a mask for the subsequent process steps. Examples of such steps are the etching of the layer support, the implantation of ions in the layer support or the precipitation of metals or other materials on the layer support.

Examples 1 to 10 which follow demonstrate the suitability of the mixture according to the invention for recording materials in microlithography, using high-energy radiation. The superiority of the mixtures according to the invention over the state of the art is demonstrated by reference to Comparison Examples 11 and 12.

In the examples, the quantities are as a rule stated as parts by weight (p.b.w.). Unless otherwise stated, percentage figures and quantitative ratios are to be understood as being in weight units.

EXAMPLE 1

A coating solution was prepared from
6.0 p.b.w. of a styrene/p-hydroxystyrene copolymer (molar ratio 30:70) having a mean molecular weight of 27,000,
1.5 p.b.w. of a cresol/formaldehyde novolak having a softening range from 105° to 120° C. and
2.0 p.b.w. of 4-(toluene-4-sulfonyloxy)benzaldehyde bis(2-phenoxyethyl)acetal (Compound No. 1) in
42 p.b.w. of propylene glycol monomethyl ether-acetate.

The solution was filtered through a filter of 0.2 $\mu$m pore diameter and whirler-coated at 3,500 rpm onto a wafer treated with an adhesion promoter (hexamethyldisilazane). After drying for 1 minute at 100° C. on a hot plate, a layer thickness of 1.0 $\mu$m was obtained.

The recording material was exposed imagewise under an original to the UV radiation of a xenon-mercury vapor lamp (using a filter with a transmission from 240 to 260 nm) with an energy of 80 mJ/cm$^2$ and stored for about 30 minutes at room temperature before development.

The recording material was developed using a 0.3N alkaline developer of the following composition:
5.3 p.b.w. of sodium metasilicate $\times$ 9 H$_2$O,
3.4 p.b.w. of trisodium phosphate $\times$ 12 H$_2$O,
0.3 p.b.w. of sodium dihydrogen phosphate and 191 p.b.w. of deionized water.

After a developing time of 60 seconds, this gave a defect-free, positive image of the mask with steep resist flanks, structures of <0.7 μm being resolved in true detail. An examination of the flanks of the resist profiles by means of scanning electron microscopy proved that these were aligned virtually perpendicular to the substrate surface.

EXAMPLE 2

A coating solution was prepared from
7.5 p.b.w. of a styrene/p-hydroxystyrene copolymer (molar ratio 20:80) having a mean molecular weight of 32,000 and
2.0 p.b.w. of 3,4-bis(toluene-4-sulfonyloxy)benzaldehyde bis(2-succinimidoethyl)acetal (Compound No. 3) in
42 p.b.w. of propylene glycol monomethyl ether acetate.

The solution was filtered through a filter of 0.2 μm pore diameter and whirler-coated at 3,000 rpm onto a wafer treated with an adhesion promoter (hexamethyldisilazane). After drying for 1 minute at 100° C. on the hot plate, a layer thickness of 1.22 μm was obtained.

The recording material was exposed imagewise under an original to the UV radiation of a xenon-mercury vapor lamp at 240 to 260 nm with an energy of 76 mJ/cm$^2$, stored for about 30 minutes at room temperature and then processed using the developer described in Example 1.

After a developing time of 60 seconds, this gave a defect-free image of the mask with high flank stability, here again structures of <0.7 μm were resolved in true detail.

EXAMPLE 3

A wafer produced according to Example 1 was irradiated under an original with KrF-excimer laser radiation of 248 nm wavelength with an energy of 100 mJ/cm$^2$. After development, an image true to the original was obtained.

EXAMPLE 4

A coating solution was prepared from
7.5 p.b.w. of the copolymer indicated in Example 2 and
2.0 p.b.w. of 4-(toluene-4-sulfonyloxy)benzaldehyde bis(2-phenoxyethyl)acetal (Compound No. 1) in
42 p.b.w. of propylene glycol monomethyl ether-acetate.

The solution was filtered through a filter of 0.2 μm pore diameter and whirler-coated at 3,100 rpm onto two wafers in total, and treated with an adhesion promoter (hexamethyldisilazane). After drying for 1 minute at 100° C. on a hotplate, a layer thickness of 1.08 μm was obtained in both cases.

One of the coated wafers was exposed imagewise under an original to the UV radiation of an xenon-mercury vapor lamp at 240 to 260 μm with an energy of 80 mJ/cm$^2$, heated for 75 seconds to 100° C. and then processed using a developer which was composed of 3% tetramethylammonium hydroxide and 97% deionized water.

After a developing time of 60 seconds, this gave a defect-free image of the mask with high flank stability, here again structures of <0.7 μm were resolved in true detail.

The second wafer was exposed, heat-treated and developed as described above after 14 days. Virtually the same results as described above were obtained. This means that the mixture applied in the dried form to a substrate has excellent stability.

EXAMPLE 5

A coating solution was prepared from
7.5 p.b.w. of a 3-methyl-4-hydroxystyrene homopolymer having a mean molecular weight of 25,000 and
2.0 p.b.w. of 4-(toluene-4-sulfonyloxy)benzaldehyde-bis(2-phenoxyethyl)acetal (Compound No. 1) in
42 p.b.w. of propylene glycol monomethyl ether-acetate.

The solution was filtered through a filter of 0.2 μm pore diameter and divided into two equal parts. One part was whirler-coated at 3,100 rpm onto a wafer treated with an adhesion promoter (hexamethyldisilazane). After drying for 1 minute at 100° C., a layer thickness of 1.08 μm was obtained.

The recording material was exposed imagewise under an original to the radiation of a xenon-mercury vapor lamp at 240 to 260 nm with an energy of 60 mJ/cm$^2$, heated for 75 seconds at 100° C. and then processed using the developer described in Example 4.

After a developing time of 60 seconds, this gave a defect-free image of the mask with high flank stability, here again structures of <0.7 μm were resolved in true detail.

The second part was subjected to the same procedure after storage for 20 weeks in the refrigerator. Identical results were obtained, which shows that the mixture has an extraordinarily high stability in solution.

EXAMPLE 6

A coating solution was prepared from
7.5 p.b.w. of the copolymer indicated in Example 2 and
2.0 p.b.w. of 4-methanesulfonyloxybenzaldehyde bis[2-(N-propylcarbamoyl)ethyl]acetal (Compound No. 2) in
42 p.b.w. of propylene glycol monomethyl etheracetate.

The solution was filtered through a filter of 0.2 μm pore diameter and whirler-coated at 3,100 rpm onto a wafer treated with an adhesion promoter (hexamethyldisilazane). After drying at 100° C. for 1 minute, a layer thickness of 1.08 μm was obtained.

The recording material was exposed imagewise under an original to the UV radiation of a xenon-mercury vapor lamp at 240 to 260 nm with an energy of 60 mJ/cm$^2$, heated for 75 seconds at 100° C. and then processed using the developer described in Example 1.

After a developing time of 60 seconds, this gave a defect-free image of the mask with high flank stability, here again structures of <0.7 μm were resolved in true detail.

EXAMPLE 7

The experiment of Example 4 was repeated twice, but instead of heating for 60 seconds at 100° C., heating was carried out for 90 seconds at 90° C. and for 60 seconds at 110° C., respectively. In both cases, the results were virtually identical and were the same as those described in Example 4, which means that the recording material according to the invention has a wide processing latitude.

EXAMPLE 8

A coating solution was prepared from 7.5 p.b.w. of a styrene/maleimide copolymer (molar ratio 1:1) having a softening range from 165° to 180° C. and 2.0 p.b.w. of 3,4,5-tris(toluene-4-sulfonyloxy)benzaldehyde bis(3-phenylpropyl)acetal (Compound No. 4) in 42 p.b.w. of cyclohexanone.

The solution was filtered through a filter of 0.2 μm pore diameter and whirler-coated at 3,700 rpm onto a wafer treated with an adhesion promoter (hexamethyldisilazane). After drying for 1 minute at 100° C. a layer thickness of 0.98 μm was obtained.

The recording material was exposed imagewise under an original to the radiation of a xenon-mercury vapor lamp at 240 to 260 nm with an energy of 120 mJ/cm² and heated for 60 seconds at 90° C.

The recording material was developed using a 0.02N aqueous solution of tetramethylammonium hydroxide, the exposed areas were being detached without residues within 60 seconds.

Once again, a defect-free image of the mask with steep resist flanks was obtained. The loss in the dark was less than 20 nm; even structures smaller than 0.7 μm were resolved in true detail.

EXAMPLE 9

A coating solution was prepared from 7.5 p.b.w. of the copolymer indicated in Example 8 and 2.0 p.b.w. of 2-(toluene-4-sulfonyloxy)benzaldehyde) bis(3-phenylpropyl)acetal (Compound No. 7) in 42 p.b.w. of propylene glycol monomethyl ether acetate.

The solution was filtered through a filter of 0.2 μm pore diameter and whirler-coated at 3,500 rpm onto a wafer treated with an adhesion promoter (hexamethyldisilazane). After drying for 1 minute at 100° C., a layer thickness of 1.00 μm was obtained.

The recording material was exposed imagewise under an original to the radiation of a xenon-mercury vapor lamp at 240 to 260 nm with an energy of 67 mJ/cm² and heated for 60 seconds at 110° C.

The recording material was developed using a 0.02N aqueous tetramethylammonium hydroxide solution. The exposed areas were detached without residues within 60 seconds and an image of the original in true detail was obtained. The edge steepness of the image was excellent.

EXAMPLE 10

A coating solution was prepared from 7.5 p.b.w. of the copolymer described in Example 2 and 2.0 p.b.w. of trisphenethyl 4-methanesulfonyloxyortho-benzoate in 42 p.b.w. of propylene glycol monomethyl ether-acetate.

The solution was filtered through a filter of 0.2 μm pore diameter and whirler-coated at 3,500 rpm onto a wafer treated with an adhesion promoter (hexamethyldisilazane). After drying for 1 minute at 100° C. a layer thickness of 1.04 μm was obtained.

The recording material was exposed imagewise under an original to the radiation of a xenon-mercury vapor lamp at 260 nm with an energy of 45 mJ/cm² and then stored for 20 minutes at room temperature.

The recording material was developed using a 0.27N aqueous solution of tetramethylammonium hydroxide. The exposed areas were detached without residues within 60 seconds, and an image of the original in true detail was obtained. Lines and gaps down to 0.5 μm were reproduced true to the mask. It was found that the solution of the material as produced still gave reproducible lithographic results identical to the first tests even after storage in the dark for 6 weeks.

EXAMPLES 11 AND 12 (Comparison Examples)

The resist formulation of Example 2 was modified in such a way that instead of 2.0 p.b.w. of Compound No. 3, 0.2 p.b.w. of the compounds (known as acid generators), triphenylsulfonium hexafluorophosphate (Example 11) or 4-(2-nitrobenzyl) tosylate (Example 12) were added to the mixture. After coating and drying, it was found that the formulation of Example 11 is about 10% more sensitive than the mixture according to the invention of Example 2 to KrF-excimer laser light of 248 nm wavelength under identical process conditions, while the sensitivity of the formulation of Example 12 did not differ from that of Example 2.

When the onium salt (Example 11) was used, however, structures having a so-called "coating foot" were obtained, i.e., residues of the resist adhered to the substrate in the exposed areas. When the tosyl ester was used (Example 12), surface crosslinkings were visible which partially overlapped the bared substrate surfaces. In both cases, acceptable structuring was thus not obtainable.

What is claimed is:

1. A positive-working radiation-sensitive mixture which comprises
  a. a polymeric binder which is insoluble in water and soluble or at least swellable in aqueous alkaline solutions, and
  b. a compound, which generates a strong acid under the action of actinic radiation and which has at least one acid-cleavable C—O—C bond wherein the compound is of the formula

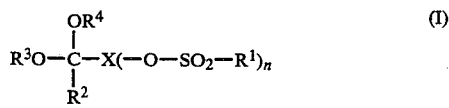

in which
  $R^1$ is an unsubstituted or substituted alkyl, fluorinated alkyl, perfluoralkyl or aryl radical,
  $R^2$ is a hydrogen atom, an unsubstituted or substituted alkyl radical, or an unsubstituted or substituted aryl radical, $(R^1—SO_2—O—)_nX—$, or $R^3O—$,
  $R^3$ and $R^4$ are identical or different and are unsubstituted or substituted alkyl, cycloalkylalkyl, cycloalkenylalkyl or aralkyl radicals, in which 1 to 3 aliphatic $CH_2$ or CH groups are optionally replaced by one or more of $NR^5$, O, S, CO, CO—O, CO—NH, O—CO—NH, CO—NH—CO, NH—CO—NH, $SO_2$, $SO_2$—O or $SO_2$—NH, or unsubstituted or substituted alkenyl, alkynl, cycloalkyl or mutually linked to form an unsubstituted or substituted heterocyclic ring,
  $R^5$ is an acyl radical,
  n is an integer from 1 to 3, and X is an alkylene, cyloalkylene, or arylene group if n is 1 or X is a(n+1)-valent radical of an alkane, cycloalkane, or arena if n is 2 or 3.

2. A radiation-sensitive mixture as claimed in claim 1, wherein $R^1$ is selected from the group consisting of a fluorinated alkyl group and a perfluoroalkyl group.

3. A radiation-sensitive mixture as claimed in claim 1, wherein $R^1$ is an alkyl radical having 1 to 6 carbon atoms, or an aryl radical having 6 to 12 carbon atoms, optionally substituted with one or more substituents selected from the group consisting of halogen, alkyl, fluorinated alkyl, alkoxy, nitro, and cyano, and $R^2$ is a hydrogen atom or an $R^3O$ radical.

4. A radiation-sensitive mixture as claimed in claim 2, wherein $R^1$ has 1 to 6 carbon atoms and $R^2$ is a hydrogen atom or an $R^3O$ radical.

5. A radiation-sensitive mixture as claimed in claim 1, wherein $R^3$ and $R^4$ are identical or different and are alkyl or arylkyl groups, each having up to 15 carbon atoms.

6. A radiation-sensitive mixture as claimed in claim 1, wherein $R^2$ is a hydrogen atom, and X is an aromatic six-membered ring.

7. A radiation-sensitive mixture as claimed in claim 1, wherein $R^3$ and $R^4$ form a heterocyclic ring selected from a 1,3-dioxolane or 1,3-dioxane ring.

8. A radiation-sensitive mixture as claimed in claim 1, wherein X is an alkylene group having 2 to 10 carbon atoms, a cycloalkylene group having 4 to 10 carbon atoms, or an arylene group having 6 to 12 carbon atoms.

9. A radiation-sensitive mixture as claimed in claim 1, wherein (b) is sensitive to light of a wavelength from 190 to 350 nm.

10. A radiation-sensitive mixture as claimed in claim 1, which contains (b) in a concentration from 2 to 60% by weight, based on the total weight of solids in the mixture.

11. A radiation-sensitive mixture as claimed in claim 1, wherein (a) has an extinction of less than 0.5 $\mu m^{-1}$ in the wavelength region of the sensitivity of (b).

12. A radiation-sensitive mixture as claimed in claim 1, wherein the binder comprises a polymer having at least one phenolic hydroxy group.

13. A radiation-sensitive mixture as claimed in claim 1, which contains (a) in a concentration from 40 to 98% by weight, based on the total weight of solids in the mixture.

14. A radiation-sensitive recording material comprising a support and a radiation-sensitive layer, wherein said radiation-sensitive layer is comprised of a radiation-sensitive mixture as claimed in claim 1.

15. A method for producing a radiation-sensitive recording material as claimed in claim 14 which comprises applying said radiation-sensitive layer to said support.

16. A method as claimed in claim 15, comprising dissolving said mixture in a solvent to form a solution, applying the resulting solution to said support, and removing said solvent.

17. A method as claimed in claim 15, which comprises first applying said radiation-sensitive layer to a temporary support, and then applying said support to said radiation-sensitive layer, and then optionally removing said temporary support.

18. A radiation-sensitive mixture as claimed in claim 1, wherein the polymeric binder contains at most 30% by weight of novolak resins.

19. A radiation-sensitive mixture as claimed in claim 1, wherein the polymeric binder contains a polymer of at least one monomer selected from the group consisting of p-hydroxystyrene and 3-methyl-4-hydroxystyrene.

* * * * *